United States Patent
Linder et al.

(10) Patent No.: US 7,078,192 B2
(45) Date of Patent: Jul. 18, 2006

(54) METHOD FOR IMMOBILIZATION OF POLYPEPTIDES

(75) Inventors: Markus Ben Linder, Helsinki (FI); Tiina Hannele Nakari-Setälä, Espoo (FI); Merja Elisa Penttilä, Helsinki (FI); Hans Erik Söderlund, Espoo (FI)

(73) Assignee: Valtion Teknillinen Tutkimuskeskus (FI)

( * ) Notice: Subject to any disclaimer, the term of this patent is extended or adjusted under 35 U.S.C. 154(b) by 52 days.

(21) Appl. No.: 10/483,961

(22) PCT Filed: Jul. 12, 2002

(86) PCT No.: PCT/FI02/00633

§ 371 (c)(1),
(2), (4) Date: Jun. 28, 2004

(87) PCT Pub. No.: WO03/008453

PCT Pub. Date: Jan. 30, 2003

(65) Prior Publication Data

US 2004/0235050 A1    Nov. 25, 2004

(30) Foreign Application Priority Data

Jul. 16, 2001    (FI) ................... 20011550

(51) Int. Cl.
*C12P 21/02*    (2006.01)
*C07H 21/04*    (2006.01)

(52) U.S. Cl. .................. 435/69.7; 536/23.74
(58) Field of Classification Search ............ None
See application file for complete search history.

(56) References Cited

U.S. PATENT DOCUMENTS 5,849,506 A    12/1998    Baekkeskov et al.
6,210,929 B1    4/2001    Schlokat et al.

FOREIGN PATENT DOCUMENTS

WO    WO 8803563    5/1988
WO    WO 9325533 A1    12/1993
WO    WO 0040968 A1    7/2000
WO    WO 00/58342    * 10/2000
WO    WO 0058342 A1    10/2000
WO    WO 0059945 A1    10/2000
WO    WO 0134902    5/2001
WO    WO 0179559    10/2001

OTHER PUBLICATIONS

Woston and de Vocht, Biochimica et Biophysica Acta 1469: 79-86 (2000), "Hydrophobins, the fungal coat unravelled".*
Appl Mixcrobiol Biotechno 1, vol. 56, pp. 1-8, Sep. 2001, published on line: May 19, 2001, K. Scholtemeiger et al: "Fungal hydrophobins in medical and technical applications", pp. 1-8, see p. 3, 2$^{nd}$ column and p. 6, 1$^{st}$ column, last paragraph.
Trends in Plant Science, vol. 1, No. 1, Jan. 1996, Joseph G.H. Wessels: "Fugal hydrophobins: Proteins that function at an interface", p. 9-15, see especially p. 12, 1$^{st}$ paragraph, and p. 14, the conclusion.
Synthetic Peptides as Receptors in Affinity Sensors: A Feasibility Study, Dave J. van den Heuvel et al. Analytical biochemistry 215, pp. 223-230, 1993.
Surface Modifications Created by Using Engineered Hydrophobins: Karin Scholtmeijer et al., Applied and Environmental Microbiology, Mar. 2002, pp. 1367-1373 XP-001120017 vol. 68, No. 3.
Ianelli et al, *Journal of Immunology,* 159(8):3910-3920 (1997).
Regimbald et al, *Cancer Research,* 56:4244-4249 (1996).
Scholtmeijer et al, *Appl. Microbiol Biotechnol.,* 56:1-8 (2001).

* cited by examiner

*Primary Examiner*—Jon Weber
*Assistant Examiner*—Anand U. Desai
(74) *Attorney, Agent, or Firm*—Sughrue Mion, PLLC (57) ABSTRACT

The present invention relates to immobilization of fusion proteins to surfaces. According to this invention a fusion polypeptide comprises an adhesion polypeptide fused to a preselected polypeptide. Specifically the method takes advantage of the spontaneous immobilization properties of the adhesion polypeptide part of the fusion protein.

20 Claims, 9 Drawing Sheets

METHOD FOR IMMOBILIZATION OF POLYPEPTIDES

This Application is a 371 of PCT/FI02/00633, filed Jul. 12, 2002, the disclosure of which is incorporated herein by reference.

BACKGROUND OF THE INVENTION

1. Field of the Invention

The present invention relates to a novel method for immobilizing polypeptides of interest and to an immobilized polypeptide. In particular, the invention provides a method for immobilizing fusion polypeptides or proteins to surfaces by fusing said polypeptides to adhesion polypeptides or proteins which have the capability of binding to the surface.

2. Description of Related Art

Protein immobilization is important for many diagnostic and biosensor applications and in, for example, immobilized enzyme reactors. The quality and properties of the adsorbed layer is often of importance for the performance of the application. Often immobilization is achieved by chemical cross-linking with glutaraldehyde (or a similar reagent), spontaneous adsorption (physical adsorption), or by coupling to reactive groups on a surface (for example amine-reactive groups). The drawback of these methods is often that they are difficult to control and may involve loss of activity of the immobilized protein. In physical adsorption loss of activity is due to denaturation of the target protein and when using cross-linking or coupling it is due to new chemical bonds that either restrict the accessibility of the protein or alter the chemical properties of the target protein. Additionally, these immobilization methods do not offer a general way of orienting the target protein in any desired fashion.

Protein monolayer formation has been described using the Langmuir-Blodgett technique, in which molecules are mechanically forced together by compression on the surface of water using a special apparatus, and then transferred onto a support. For some proteins, layers can be manufactured either directly in this manner or, for example, first making a biotinylated lipid layer, to which an avidin layer is bound and to which in turn a biotinylated target protein can be bound. The problem involved in this technique is that most proteins do not form layers at the interphase which can be transferred, and that special equipment is needed.

It is of interest that a rapid and easy immobilization method is developed. Preferred properties of an immobilization method would, for example, be that there is no need for special equipment or that there is no need for formation of monolayers. A very important property of an immobilization method is that the protein of interest is not denatured. It is of advantage also that in the method there are no chemical cross linking steps, because that would increase the probability of denaturation of the protein.

Preferred properties would furthermore be that the protein of interest can be oriented in a desired fashion to the solid phase, that the production of the protein to be immobilized is easy and that the protein surface layer is durable. It is also of practical value that layers which have a certain density of the polypeptide of interest, can be made. It can also be of value that the immobilized protein can be easily removed from the solid phase under certain conditions.

Fusion polypeptides attached to a solid carrier are known from WO 8803563, WO 0179559, U.S. Pat. No. 6,210,929, WO 0134902, WO 9325533, U.S. Pat. No. 5,849,506, from Regimbald et al. (1996) and Janelli et al. (1997). WO 0058342 describes a fusion polypeptide, the other party of which is an adhesion polypeptide.

It is known that proteins used as antigens in enzyme-linked immunosorbent assays (ELISA) or in similar assays where a polypeptide is bound to a surface, can lose or acquire changed antigen binding properties or other properties, and thus cause problems in the assay. In one way to avoid this, the antigen needs to be biotinylated and then bound to a surface which previously has been coated with avidin or streptavidin in an extra step.

Wessels (1997) has suggested that hydrophobins may be used as an intermediate layer to attach cells, proteins, such as antibodies, and small ligands to hydrophobic surfaces. SC3 hydrophobin has been shown to coat a hydrophobic gold surface. It was suggested that at the exposed hydrophilic side of surface-bound SC3 film, mannose residues can be oxidized with periodic acid without disturbing the binding to the gold, while the generated aldehyde groups were suggested to be coupled to amino groups of a protein by a Schiff based reaction. This approach has the disadvantage that new chemical bonds are formed that may either restrict the accessibility of the protein or alter the chemical properties of the target protein.

SUMMARY OF THE INVENTION

It is the aim of the present invention to eliminate the problems of the prior art and to provide a novel method for immobilizing polypeptides or proteins, in which method the polypeptide or protein of interest retains an essential amount of its biological function or activity.

In particular, one object of this invention is a process for immobilizing polypeptides or proteins, which comprises the steps of fusing a nucleotide sequence encoding an adhesion polypeptide or protein to a nucleotide sequence encoding a polypeptide or protein of interest, transferring and expressing the fusion construction in a host under suitable conditions and immobilizing the fusion polypeptide or protein directly from the growth medium or from purified or from partly purified growth medium or from broken host cells, or from unpurified, purified or partly purified protein solution, to a solid surface, through the adhesion polypeptide or protein.

The process for immobilizing proteins according to the present invention is mainly characterized by what is stated in the characterizing part of claim 1.

Another object of this invention is an immobilized polypeptide or protein, which comprises a fusion polypeptide or protein immobilized to a solid surface. The fusion polypeptide or protein comprises at least two parts: the polypeptide of interest and an adhesion polypeptide. The adhesion polypeptide is preferably hydrophobin or a hydrophobin like protein. The fusion protein is immobilized to a solid surface through the adhesion polypeptide or protein. The adhesion protein part of the fusion protein is capable of spontaneously immobilizing to a solid surface.

The immobilized polypeptide according to the present invention is mainly characterized by what is stated in the characterizing part of claim 22.

Considerable advantages are obtained with the aid of the present invention. One important advantage is that the immobilization method prevents loss of activity of the polypeptide of interest, in other words, the polypeptide of interest retains an essential amount of its biological activity or function in the method. In the conventional immobilization methods the biological activity or function is often partly or completely lost.

Another important advantage is that the adsorption is spontaneous. No chemical cross-linking or coupling to reactive groups is needed in the method.

In the conventional immobilization methods the polypeptide or protein should usually be purified before immobilization. According to this invention the immobilization can be made using a crude protein preparation, thus avoiding costly and complicated purification schemes. It is even possible to immobilize proteins directly from the culture medium in which the protein has been produced.

In addition, the method gives a surface with a high density of functional polypeptides, if desired to increase, for example, the capacity of the surface. If a layer is needed having a specific surface density of the polypeptide of interest, the present invention offers an easy way to produce layers with the desired specific surface density.

One advantage is also that the method according to this invention provides the possibility to influence to the orientation of the polypeptide of interest. It may be, for example, of advantage that the polypeptide of interest is oriented out from the surface.

These and other objects, together with the advantages thereof over known immobilization methods or processes, are achieved by the present invention as hereinafter described and claimed.

BRIEF DESCRIPTION OF THE DRAWINGS

FIG. 2.

A) Binding isotherm of EGI-HFBI fusion protein to silanized glass, measured as bound enzymatic activity of the fusion protein. A first order Langmuir isotherm is fitted on the data giving a maximum bound activity of 2.8 µmol/m$^2$ (67 pmol/s) and a dissociation constant of 0.44 µM (21.8 µg/ml).

B) Corresponding isotherms showing the binding of EGIc-HFBI to TEFLON and polystyrene as compared to silanized glass. The control shows that EGIc does not bind to polystyrene in its biologically active form.

FIG. 3. Kinetics of the binding and desorption of EGIc-HFBI to silanized glass.

A) Adsorption rate without and with the presence of a ten time molar excess of free HFBI. The fusion protein is competed out from the binding at a stoichiometric proportion.

B) Desorption of EGIc-HFBI from a silanized glass surface by washing with an excess of buffer.

FIG. 6.

A) Frequency shifts as a function of time during the binding of EGIc, EGIc-HFBII and EGIc-HFBI to a silanized quartz surface in a quartz microbalance at a resonant frequency of 15 MHz. Measurements were done in static conditions. In B) the change in energy dissipation value as a function of Δf is shown. The data show that especially the HFBI fusion forms a dense and rigid layer.

DETAILED DESCRIPTION OF THE INVENTION

Definitions

For the purpose of the present invention, the term "immobilize" means that a polypeptide shows increased concentration at a surface under desired conditions. In particular, a polypeptide of interest shows at least 10 times, preferably at least 100 times, more preferably at least 1000 times higher concentration at a surface than in the liquid at a distance from the surface. However, it depends on the application, when a sufficient immobilization or adsorption to a surface has taken place. Although the immobilization or adsorption would not be very strong it may be sufficient for a certain application.

The term "adsorption" means here the process of an atom or molecule becoming attached to a solid surface.

The term "desorption" means here the opposite event to "adsorption".

"A fusion polypeptide of protein" stands for a polypeptide which contains at least two polypeptide parts which have been combined together by recombinant DNA techniques.

"An adhesion polypeptide" means here a polypeptide, which functions in the fusion polypeptide construction as hydrophobins or hydrophobin like proteins. An adhesion polypeptide is capable of immobilizing to a solid surface.

In the fusion construction is used the adhesion polypeptide or a functional part thereof. Functional part of the adhesion polypeptide means such part of the adhesion polypeptide which in the fusion construction is capable of immobilizing to a solid surface.

The fusion construction comprises preferably also a linker between the polypeptide of interest and the adhesion polypeptide.

The term "hydrophobin" means here a polypeptide which has resemblance in properties or sequence to the described peptides HFBI, HFBII, SRHI or SC3.

By the term "HFBI like", "HFBII like", "SRHI like" or "SC3 like" is meant here a polypeptide which has the described properties.

The present invention is meant to cover also the polypeptides HFBI, HFBII, SRHI and SC3 or polypeptides, which have the described properties and comprise amino acid sequences, which are at least 40%, preferably at least 50%, more preferably at least 60%, still more preferably at least 70% homologous at the amino acid sequence level to the mentioned polypeptides. Even more preferably are covered polypeptides, which comprise amino acid sequences, which are at least 80%, most preferably at least 90% homologous at the amino acid sequence level to the mentioned polypeptides.

By the term "polypeptide" is meant here a sequence of two or more amino acids joined together by peptide bonds. By the definition all proteins are polypeptides. The term polypeptide is used here to mean peptides and/or polypeptides and/or proteins.

"A polypeptide of interest" or "a preselected polypeptide" stands for any polypeptide which has a desirable property or which can bind any one or more molecules which are of interest. The polypeptide is selected from, but is not limited to, the group comprising: an antigen, an antibody, an enzyme, a structural protein, an adhesion protein or a regulatory protein.

"A solid surface" means here a surface or matrix to which an adhesion polypeptide, like hydrophobin, hydrophobin like or a hydrophobin modification can bind to. Preferably the solid surface is a hydrophobic surface. The solid surface may be selected from the group comprising: a silanized surface, a hydrocarbon coated surface, a polymer, such as polyeten, poly-propylen, polystyren, or TEFLON.

According to the method of this invention the fusion polypeptide can be desorbed from the surface in a controlled fashion. Preferably this is done with excess of buffer and/or octyl-glucoside detergents, such as SDS, Tween 20, $C_{12-18}$ $EO_5$ or octyl-glucoside.

The term "biological function" or "biological activity" means here any property which is dependent on the covalent structure or the conformation of the polypeptide. The biological activity may mean for example enzymatic activity, catalytic activity, antigenic properties or regulatory functions.

By the expression "retaining essentially the biological function or activity" is meant here that the polypeptide or protein in question retains at least 50%, preferably at least 60%, more preferably at least 70% of its biological function or activity. Even more preferably the polypeptide or protein in question retains at least 80% and most preferably at least 90% of its biological function or activity. In the most preferred embodiment of this invention the polypeptide or protein in question retains even 99% or more of its biological function or activity.

By "bioactive surface" is meant a surface which has a biological function brought about by a polypeptide bound to a solid surface.

According to this invention it is possible to produce polypeptide layers with a desired specific surface density. This can be achieved by immobilizing a specific amount of the fusion polypeptide comprising the polypeptide of interest together with a specific amount of free adhesion polypeptides.

According to this invention the it is also possible to produce polypeptide layers with a desired combination of two or more preselected polypeptides. This is achieved by immobilizing fusion polypeptides comprising different preselected polypeptides to the same solid surface.

The fusion polypeptide can be produced in a fungal or yeast host, selected from the group comprising *Trichoderma* spp, *Aspergillus* spp. *Neurospora* spp., *Fusarium* spp., *Penicillium* spp., *Humicola* spp., *Tolypocladium geodes*, *Kluyveromyces* spp., *Pichia* spp., *Hansenula* spp., *Candida* spp., *Yarrowia* spp, *Schizosaccharomyces* ssp, *Saccharomyces* spp. and *Schizophyllum* spp. Preferably the fusion polypeptide is produced in a *Trichoderma* host.

The immobilization process can be carried out at the temperature 5 to 40° C., preferably it is carried at 20° C. to 35° C. The immobilization process can be carried out at the at pH 3 to 7, preferably it is carried out at pH 4 to 6. The immobilization process can be carried out at ionic strength of 0.1 to 2 M, preferably it is carried out at ionic strength 0.5 to 1M.

"Hydrophobins" are a group of proteins, which so far only have been found in filamentous fungi where they seem to be ubiquitous. They are secreted proteins which in some cases are found in the culture medium as monomers, and migrating to interfaces where they self assemble to form thin surface layers, but they are also found bound to the hyphae. Hydrophobins are also characterized by their high surface activity. The layer formed by the hydrophobin SC3 from *Schizophyllum commune* has been extensively characterized, and has the property of changing the surface hydrophobicity so that it turns a hydrophilic surface hydrophobic and a hydrophobic surface hydrophilic (Wosten, de Vries et al. 1993)(Martin, Cannon et al. 2000). The SC3 layer is easily visualized by electron microscopy and is characterized by its tightly packed rodlet pattern, and is therefore often called a rodlet layer (Wessels 1997). The SC3 layer is very stable, and only very harsh chemicals such as pure trifluoroacetic or formic acid can dissolve it. For example heating in a solution of sodium dodecyl sulfate (SDS) does not affect the layer (de Vries, Fekkes et al. 1993). It has also been shown that large conformational changes can be associated with the assembly and adsorption (de Vocht, Scholtmeijer et al. 1998).

Comparison of hydropathy plots forms the basis of dividing the hydrophobins into two classes, I and II. The two classes share several general properties, but seem to significantly differ in some aspects such as the solubility of their assemblages. Whereas the class I assemblages are highly insoluble, the class II hydrophobin assemblages and adsorbed surface layers seem sometimes to dissociate more easily, for example by 60% ethanol, SDS, or by applying pressure. No rodlet type surface structures have this far been reported for class II hydrophobins, and in many ways the class II hydrophobins seem to be less extreme in their behavior (Wosten and de Vocht 2000). Although the distinction between classes can be made by comparison of primary structure, no explanation of the difference in properties can be made on the amino acid level.

In hydrophobins the most prominent feature is the pattern of eight Cys residues which form the only conserved primary structure in the hydrophobin-families, but also hydrophobins in which this pattern has not been conserved have been described (Lora, de la Cruz et al. 1994). Hydrophobins can also differ in modular composition, so that they contain different mumbers of repeating hydrophobin units (De Vries, Moore et al. 1999). Otherwise hydrophobins show considerable variation in primary structure. HFBI and HFBII are two class II hydrophobins from the fungus *Trichoderma reesei* and are quite similar with a sequence identity of 66%. The published data on class I and II hydrophobins show that there is a functional division between the classes which mainly seems to involve the structure and solubility of their aggregates. Systematic investigations of surface binding of class II hydrophobins have not been reported before, but adsorption of the class I hydrophobin SC3 has been characterized much more in detail. In the case of SC3 the formation of rodlet layers seem to be an essential component of the binding. Hydrophobins have been described in for example the following articles; (Wessels 1997); and (Wessels 1996). The isolation of the gene for *T reesei* HFBI has been described in (Nakari-Setala, Aro et al. 1996) and HFBII in (Nakari-Setala, Aro et al. 1997). The isolation of the srh1 gene of *T. harzianum* has been described in (Munoz, Nakari-Setala et al. 1997). Furthermore hydrophobins can be identified and cloned as described in International Patent Application PCT/FI00/00249 (WO 00/58342).

International Patent Application PCT/FI00/00249 (WO 00/58342) describes the construction and production of several hydrohobin fusion proteins. Among them is the *Trichoderma reesei* HFBI is fused to the hydrolytic enzyme EGI (endoglucanase I). This construction has been used to produce and purify large quantities of said fusion protein by an aqueous two phase extraction method.

The present invention is exemplified with studies of the adhesive properties of two fungal hydrophobin proteins, HFBI and HFBII from *T. reesei* and the hydrophobin SC3 from *Schizophyllum commune* as partners in fusion proteins. Three recombinant fusion protein constructs were made where the catalytic domain of endoglucanase EGI (EGIc) from *T. reesei* was fused to either HFBI or HFBII or SC3. Characterization was made by comparing the properties of the two fusion proteins and, as a control the isolated enzyme domain, EGIc. The main result was that HFBI can successfully be used to immobilize fusion proteins to hydrophobic surfaces with good stability, and retaining the activity of the fusion partner, as shown in examples 3, 4, 5, 6 and 7. The HFBII fusion protein binds in a different manner than HFBI as shown in examples 4 and 5. The types of hydrophobic surfaces were TEFLON, polystyrene and alkylated or silanized glass or gold. Studies of the adsorption of the isolated hydrophobins on hydrophobic surfaces by Surface Plasmon Resonance (SPR) were made as a comparison in example 4 and in co-adsorption experiments in example 5.

Desorption of bound fusion protein was studied in two types of experiments, in the enzymatic activity and the SPR experiments (Example 3 and 4). Desorption as studied by the bound enzymatic activity is slow for the HFBI fusion and in the case of the HFBII fusion it is initially quicker. Although the initial HFBII fusion off-rate is fast, a residual amount stays very stably bound. In the corresponding SPR experiment with EGIc-HFBI there is a small initial quick desorption, followed by a very slow stage.

The adsorbed HFBI-fusion protein layer is most probably a monolayer which completely covers the surface. This is indicated by the fact that a well defined saturation level achieved in the isotherm shown in FIG. 2A of example 3 and also in the SPR experiments does a saturating adsorption level form. The maximum bound level corresponded to 14 mg/m$^2$ which is in the range expected for a dense monolayer. In the quartz microbalance (QCM) experiments (example 6) the ΔD-value is low which indicates that the layer is thin and relatively rigid.

Figure 2A:
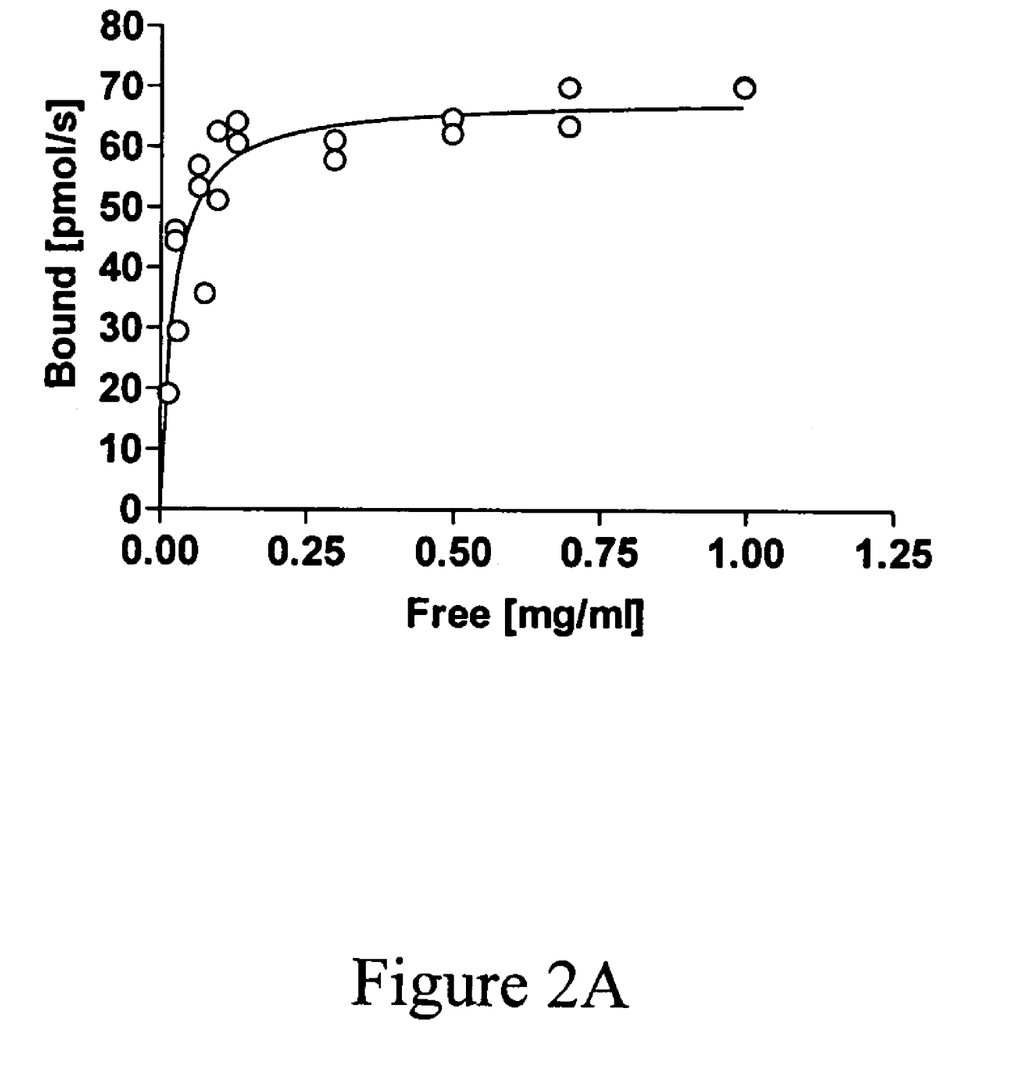
Figure 2B:
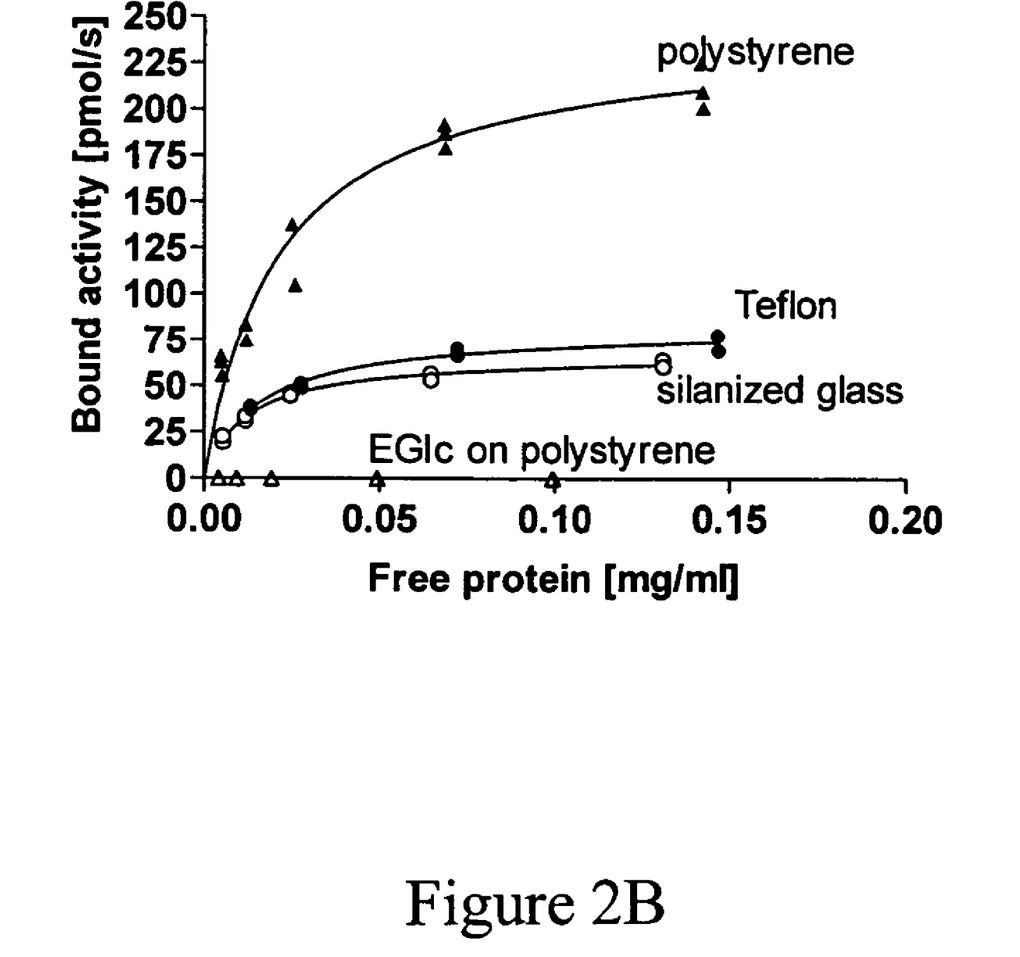

One advantage which the fusion protein approach provides in immobilization is illustrated in example 7 and in example 3 (FIG. 2B). It is shown that the binding of fusion protein keeps the polypeptide of interest functionally active, whereas activity of the spontaneously bound fraction of the free polypeptide is lost. In the examples, all of the control protein EGIc that binds becomes denatured and thus non-functional. This indicates that during fusion protein binding the molecule is bound in such a fashion that the catalytic fusion partner points outwards and does not denature on the surface, as would happen during physical adsorption.

It is also surprising that both fusion proteins and the isolated hydrophobins are water soluble up to at least 10 mg/ml, although their hydrophobic interactions seem to be so important for the binding. There is thus no need for surfactants or other additives to keep the protein soluble.

The fusion protein can be immobilized directly from the growth medium or from broken host cells to a solid surface. The fusion protein to be immobilized can also be pure. The purification can for instance be efficiently accomplished by aqueous two phase separations as described in International Patent Application PCT/FI00/00249 (WO 00/58342).

The method provides an easy way of producing immobilized protein with desired surface density of immobilized fusion protein by mixing ratios of fusion protein and free hydrophobin as shown in example 5. This property can also be utilized for producing surfaces with mixed polypeptides of interest, which sometimes is of advantage when multivalency is required in for example antibody-antigen interactions.

The invention can be used in, for example, diagnostic devices, such as strips or microtiter plates where a polypeptide of interest is immobilized. In these applications the aforementioned advantages such as ease of immobilization is of advantage. In some cases if the polypeptide of interest is small its production by recombinant DNA technique is difficult and the hydrophobin fusion partner can act as a carrier of the polypeptide.

Biosensor surfaces also represent cases where the above mentioned desired properties such as homogeneity, thickness and spontaneous adsorption are of advantage.

Creating bioactive surfaces by immobilizing biologically active polypeptides allows study of interactions of other poypeptides with the immobilized ones, and can therefore have applications in high—throughput screening, solid phase extraction or chromatographic purification. The immobilization can also have advantages in purifying the fusion protein itself.

EXAMPLE 1

Construction of Fusion Proteins

EGI from *T. reesei* is, like many cellulolytic enzymes, a modular protein. It consists of a catalytic domain in the N-terminus (368 amino acids) and a cellulose-binding domain in the C-terminus (36 amino acids). The two domains are connected by a glycosylated linker (33 amino acids). The EGIc protein used in this study is truncated form of EGI which lacks the C-terminal cellulose-binding domain and most of the connecting linker. It consists of the first 371 amino acids of EGI. The EGIc-HFBI contains the full linker but at position 403 where the cellulose-binding domain begins, the 75 amino acid HFBI (Nakari-Setala, Aro et al. 1996) was inserted instead of the cellulose-binding domain. Analogously the EGIc-HFBII has the 71 amino acid HFBII (Nakari-Setala, Aro et al. 1997) inserted instead of the cellulose binding-domain.

Recombinant DNA Constructions

The cloning of EGIc is described in (Srisodsuk, Lehtio et al. 1997), and the cloning of EGIc-HFBI and EGIc-SC3 is described in Penttilä et al. (PCT/FI00/00249, WO 00/58342). To make the strain producing EGIC-HFBII we used the vector for EGIc-HFBI (pMQ113) which carries the gene cassette under the strong cbh1 promoter, as a template. The EGIc-HFBII was constructed by replacing the hfb1 sequence in PMQ113 with the hfb2 sequence. First, the hfb2-coding region from Ala-16 to the STOP codon was amplified with PCR using the primer pair 5' CGG AG GAGCTCGACGACTTCGAGCAGCCCGAGCTGCACG CAG GCT GTC TGC CCT ACC GG (sense) and 5' TCA TTG GAT CCT TAG AAG GTG CCG ATG GC (antisense) and the vector phfb2 as a template (Nakari-Setala, Aro et al. 1997). The underlined sequence in the sense primer encodes for amino acids 413–425 in EGI. The PCR fragment was digested with SacI and BamHI, and ligated to pMQ113 which had been similarly digested. The resulting fungal expression vector, pTNS32, carried the EGIc-HFBII cassette under the regulatory control of the cbh1 promoter and terminator sequences. Prior to fungal transformation, pTNS32 was digested with EcORI and SphI to release the expression cassette.

*T. reesei* strain QM9414 was transformed according to (Penttila, Nevalainen et al. 1987) using 10 μg of digested pTNS32 together with 4 μg of pARO21 which is essentially the same as pRML$_{ex}$30 (Mach, Schindler et al. 1994) and confers resistance to hygromycin. Transformants were streaked three times on selective medium, then transferred to potato dextrose agar for sporulation. Spore suspensions were plated out on selective medium to obtain single spore colonies for further analysis. Hygromycin positive transformants were screened for production of EGIc-HFBII fusion protein by analyzing culture medium samples from microtiter plate cultivations on cellulose with HFBII specific antibodies.

EXAMPLE 2

Protein Production and Purification

EGIc was produced and purified by ion exchange chromatography as in (Srisodsuk, Lehtio et al. 1997). EGIc-HFBII (strain X77A) was grown in shake flasks in minimal medium (Penttila, Nevalainen et al. 1987) supplemented with 3% Solka floc cellulose (James River Corporation, USA) and 1.5% complex grain based nitrogen source for 7 days. It was purified from the culture medium by first desalting on a Bio-Rad P6 (Bio-Rad, USA) column with 10 mM acetate buffer pH 5.0. The desalted fraction was then loaded on a Resource Q column (Amersham Pharmacia, Sweden) and eluted with a linear gradient of 10 mM acetate pH 5.0 containing 0.2 M NaCl. As a final step the EGIc-HFBII peak fraction was then loaded on a Phenyl Sepharose (Amersham Pharmacia, Sweden) after first adding $(NH_4)_2SO_4$ to final concentration of 0.5 M. Elution was with 10 mM acetate pH 5.0. The purification was followed by running SDS-PAGE and western blotting using polyclonal antibodies raised against EGI, HFBI and HFBII.

Bioreactor cultivation of EGIc-HFBI were done with strain VTT D-99702 with 40 g/l lactose in minimal medium for 4 days in a LF7 fermenter (Chemap, Switzerland). EGIc-HFBI was purified similarly as EGIc-HFBII except that initially a surfactant two phase extraction was made and the Phenyl Sepharose step was omitted.

For adsorption experiments the buffers were exchanged with 10-DG columns (Bio-Rad). Protein concentrations were determined by adsorption at 280 nm using an extinction coefficient of 61180 for EGIc-HFBI, 60020 for EGIc and EGIc-HFBII.

EXAMPLE 3

Binding of Fusion Analyzed by Enzymatic Activity of the Polypeptide of Interest

Binding of EGIc-HFBI and the control EGIc to different surfaces was initially tested by immersing a rod into 0.5 ml of fusion protein solution in a test tube. As standard conditions for adsorption 50 mM acetate buffer at pH 5.0 was used. Addition of NaCl or $(NH_4)_3SO_4$ was used for testing the effect of ionic strength. For testing the effect of pH, glycine pH 3.0 or Hepes pH 7.0 was used. The rods were either made of glass or TEFLON and had a diameter of 2 mm with rounded tips and a length of about 3 cm. Using the same volume in the test tubes, the exposed surface of the rods was kept constant. The glass rods were either used as such or silanized with trimehylchlorosilane (T4252, Sigma) or dimethyl dichlorosilane (D3879). TEFLON rods were obtained from Cowie Technologies (UK). At certain timepoints the rods were lifted out of the solution and placed in 5 ml of 50 mM acetate buffer pH 5.0 for 2 minutes with gentle shaking. The wash was then repeated.

Figure 1:
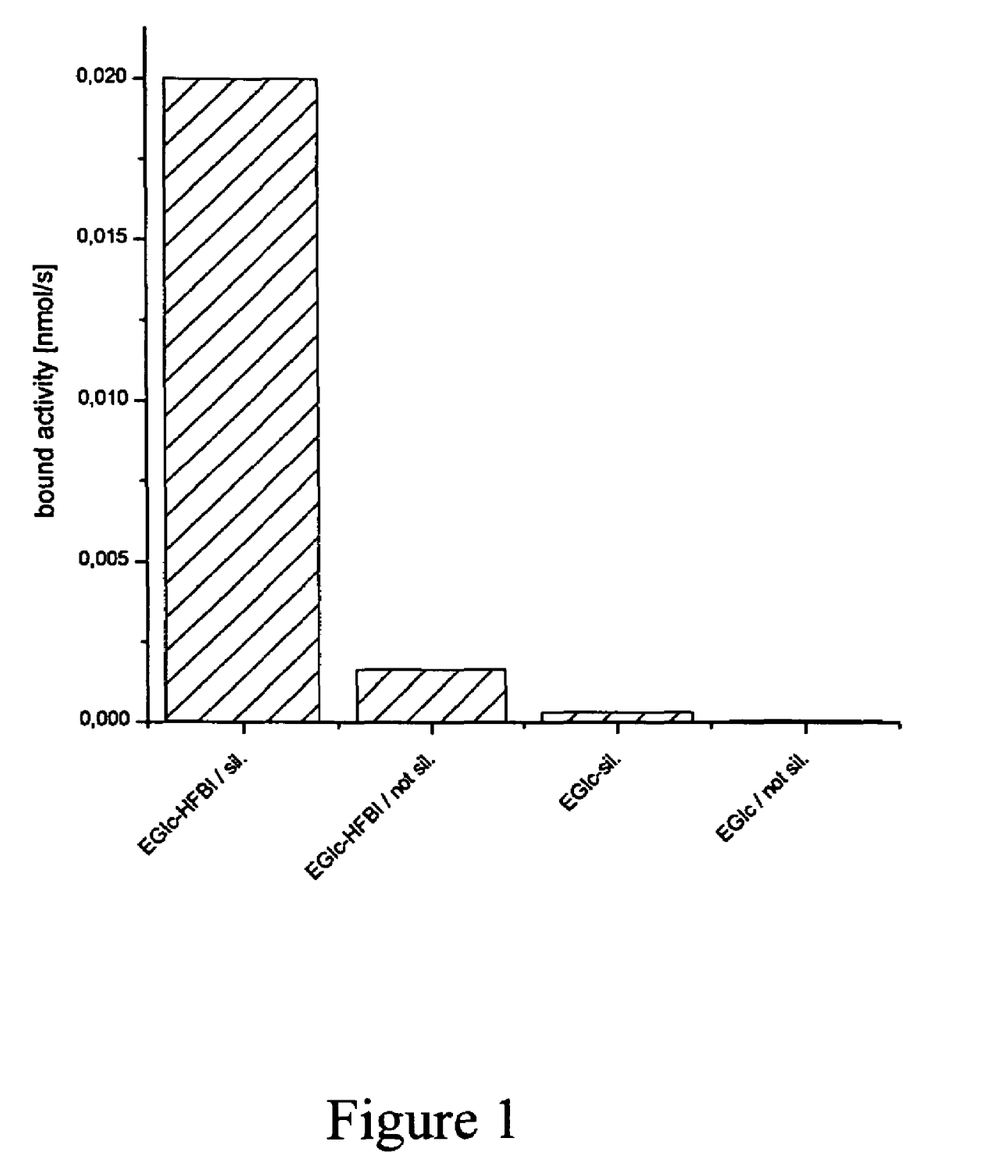
FIG. 1. Bar-graph showing the adhesion of EGIc-HFBI to a silanized and a non-treated glass surface in comparison with the EGIc control. The adhesion is measured as bound enzymatic activity of the fusion protein, and shows that the fusion with HFBI specifically causes the protein to immobilize on a hydrophobic surface.

In the enzymatic activity measurements we utilized the activity of EGI towards the soluble fluorogenic substrate 4-methylumbelliferyl β-D-cellobioside (MUG2) (M6018, Sigma) to assay the protein. Neither hydrophobin shows any enzymatic activity on this or any other known substrate. The amount of bound enzyme activity was assayed by immersing the rod into 0.5 ml of 0.5 mM MUG$_2$ for 5 min. The reaction was terminated by lifting out the rod and adding 0.5 ml 1 M NaCO$_3$. Measurement of activity in liquid samples were performed similarly. Liberated methylumelliferone was assayed by fluorescence on a 96 well reader using an excitation filter (355 nm) and emission filter (430 nm) (Multiscan, Labsystems, Finland). To make standard curves for the activity measurements, the pure reaction product 4-methylumbelliferone (M 1381, Sigma) was used. The association rate was calculated by fitting a one phase exponential association curve to the data, using Prism software (Graph Pad, USA). The results presented in FIG. 1 show that the combination of HFBI-fusion and the hydrophobic surface results in significant binding, whereas the other combinations showed much lower binding.

In order to establish the adsorption capacity, a binding isotherm was determined (FIG. 2A). The isotherm was modeled with a first order Langmuir equation. A maximum adsorption is reached at about 70 pmol/s. For quantification we determined the specific activity for EGI to 3.48 nmol s$^{-1}$ mg$^{-1}$ (22° C.). From this it can be estimated that about 14 mg m$^{-2}$ protein was immobilized on the silanized glass rods. From the isotherm data it could be estimated that the dissociation constant ($K_d$) of the EGIc-HFBI/silanized surface complex is 0.44 μM (21.8 μg/ml, Bmax=2.8 μmol/m$^2$).

Partial isotherms for the binding of fusion protein to TEFLON and polystyrene in comparison to silanized glass is shown in FIG. 2B. As shown in the figure, the EGIc control binding to polystyrene shows no bound EGI by the enzymatic activity.

The temperature dependency was tested by determining partial binding isotherms at 5, 22, 35° C. and comparing the affinity by the initial slopes of the isotherms. No significant effect of temperature was noted. Effects of changing ionic strength were determined by adding NaCl or $(NH_4)_2SO_4$. A high salt concentrations (1M) resulted in a slight increase (10–15%) of affinity. Experiments using buffers at pH 3, 5, and 7 showed a greater effect, with 25% better binding at pH 5 than at pH 3 and 40% better at pH 5 than at pH 7.

Figure 3A:
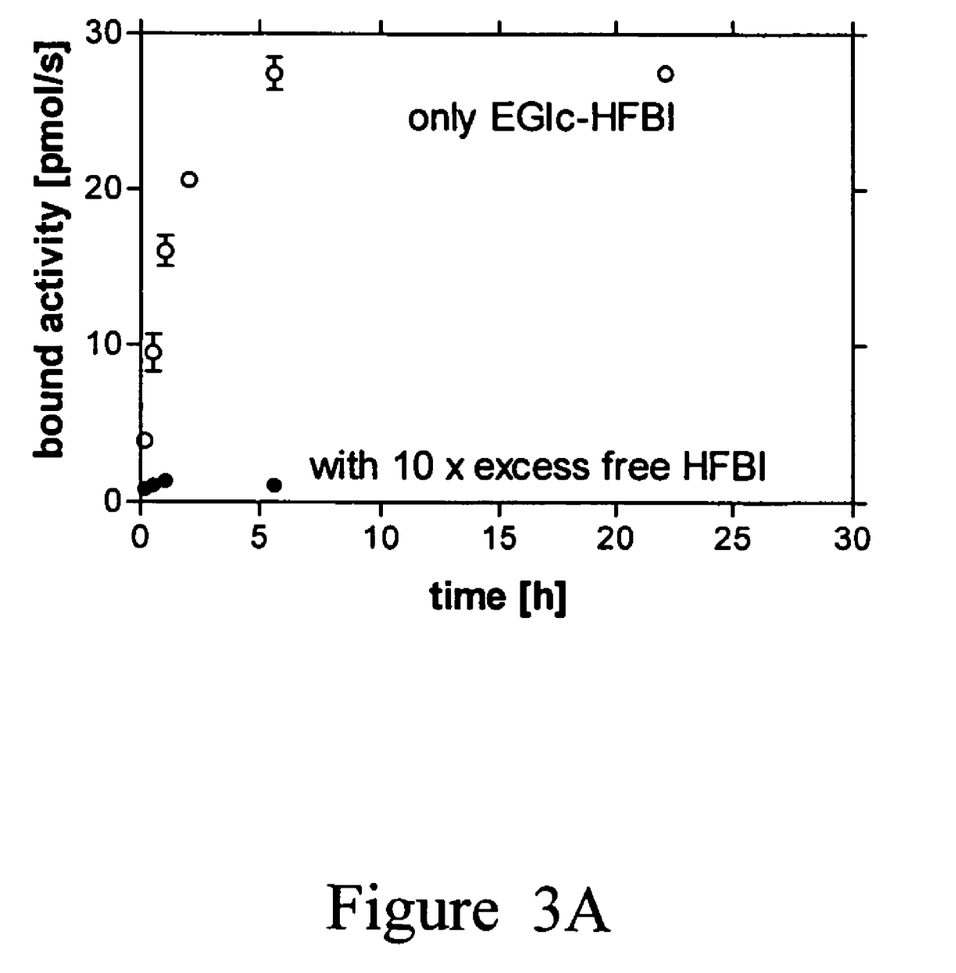
Figure 3B:
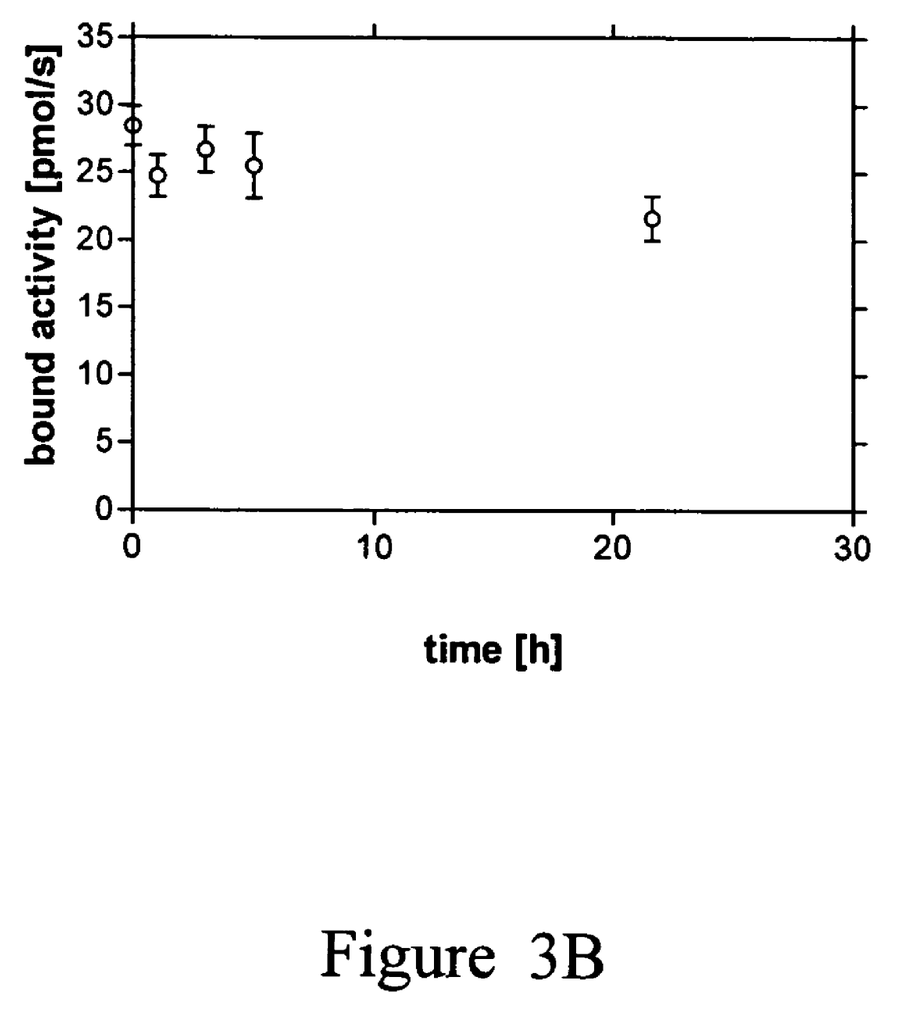

The kinetics of binding to, and desorption from silanized glass is shown in FIGS. 3A and 3B. The binding is very slow and requires over five hours to reach a steady value.

In the desorption tests, rods that had been incubated with EGIc-HFBI were washed and then incubated for different times in a large excess of buffer (50 mM acetate pH 5). A slight desorption or inactivation can be noted over 24 hours. Desorption was also studied by adding 0.5% SDS or Tween 20 to the wash buffers. Using SDS the activity disappeared instantaneously, and using Tween 20 the bound activity was reduced to 50% in 1–2 hours.

EXAMPLE 4

Binding Analysis by Surface Plasmon Resonance

Figure 4:
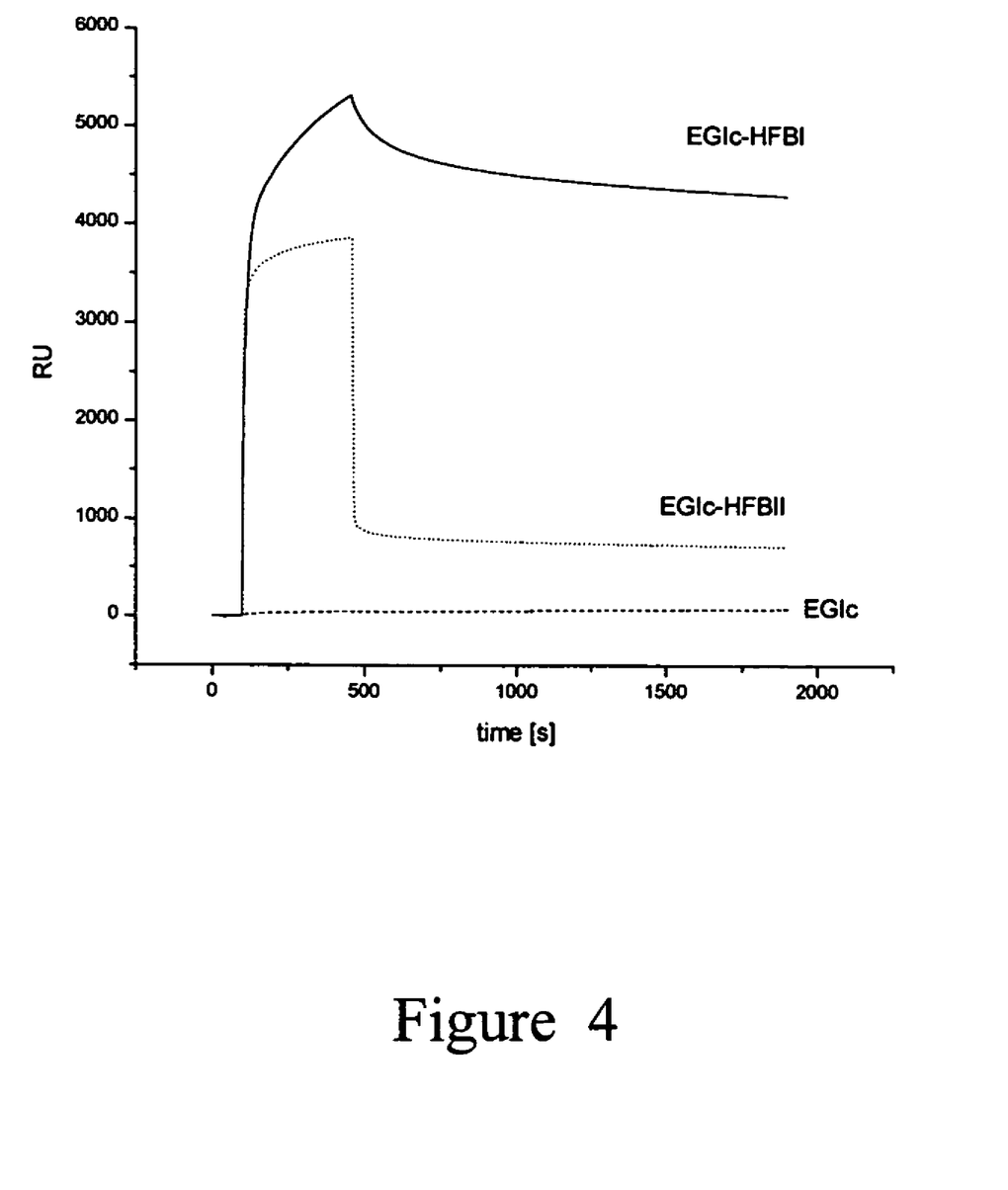
FIG. 4. Sensograms of EGIc, EGIc-HFBII and EGIc-HFBI binding to an alkylated gold surface measured by SPR. The EGIc control does not show any binding to the surface, EGIc-HFBII adsorbs during the injection but desorbs during the wash step, whereas EGIc-HFBI adsorbs during injection and shows a slow desorption during the wash.

For the study of binding by surface plasmon resonance a Biacore biosensor (Biacore, Sweden) was used. Prefabricated HPA sensor surfaces were used, which have a layer of octadecanethiol bonded to an underlying gold surface. 50 mM acetate buffer pH 5.0 was used as running buffer at 5 µl/min. The flow cells were washed with 1% octyl glucoside and washed extensively prior to sample application. The sample volume was typically 30 µl, and the desorption of protein was tested with octyl glucoside, SDS and the non-ionic surfactants Tween 20 and $C_{12-18}EO_5$, using dilutions of 10, 5 and 1 g/l and injection volumes of 5–25 µl. In FIG. 4 an example of the adsorption behavior of the two fusions and the control on an alkene thiol coated gold surface are shown. In this example the EGIc control was first injected and then the EGIc-HFBII fusion and finally the EGIc-HFBI fusion. EGIc has a negligible adsorption and does not show any response signal at this scale of magnification. EGIc-HFBII shows a fast binding during the sample injection, and a fast desorption during the wash step, whereas the HFBI fusion shows a somewhat slower binding and a very slow desorption. In other experiments, the order of injection and the number of injections was varied. When the HFBI-fusion was injected on a fresh surface, the level of bound protein was higher by the same amount that the HFBII fusion bound in the example in FIG. 4, and correspondingly the HFBII fusion did not bind if HFBI fusion was first injected. We tested desorption with the surfactants SDS, Tween 20, $C_{12-18}EO_5$ and octyl-glucoside for regeneration of the surface, and found that a 5 µl injection of SDS at a concentration of 1 g/l is able to removed the bound protein. The other surfactants did not significantly reduce the level of bound protein, although surfactant injection often resulted in an unstable signal. After regeneration, the binding of the next round of protein was similar to previous ones, but sufficiently different not to allow curve fitting and calculation of binding parameters. The possible cause for this is that the surface was damaged by the regeneration.

In SPR a phenomenon called the buffer or bulk effect is seen when the sample solution has a different refractive index from the running buffer. This means that a RU signal is seen even though there is no binding (Hashimoto 2000). In this work the bulk effect of the EGIc control protein was negligible compared with the signal produced by the two fusion proteins. It can therefore be concluded that the HFBII fusion signal is due to a real interaction, and not a bulk effect, but in which both off and on-rates are fast.

The EGIc-HFBI sample shows a slower on-rate binding and a much slower desorption rate than the EGIc-HFBII sample. The bound HFBI fusion did not desorb during extended over-night buffer washes more than 5%. It is noteworthy that the HFBII fusion attains a very stable but low level of bound protein after the initial quick desorption step. After four subsequent injections the RU level was about 4500 for EGIc-HFBI and about 900 for EGIc-HFBII. The level did not rise from this during subsequent injections even at protein concentrations over 250 µg/ml. Since the response in SPR is related to the bound mass, it is possible to estimate the amount of bound protein, by the relation that about 1000 RU corresponds to 1 mg/m².

Figure 5:
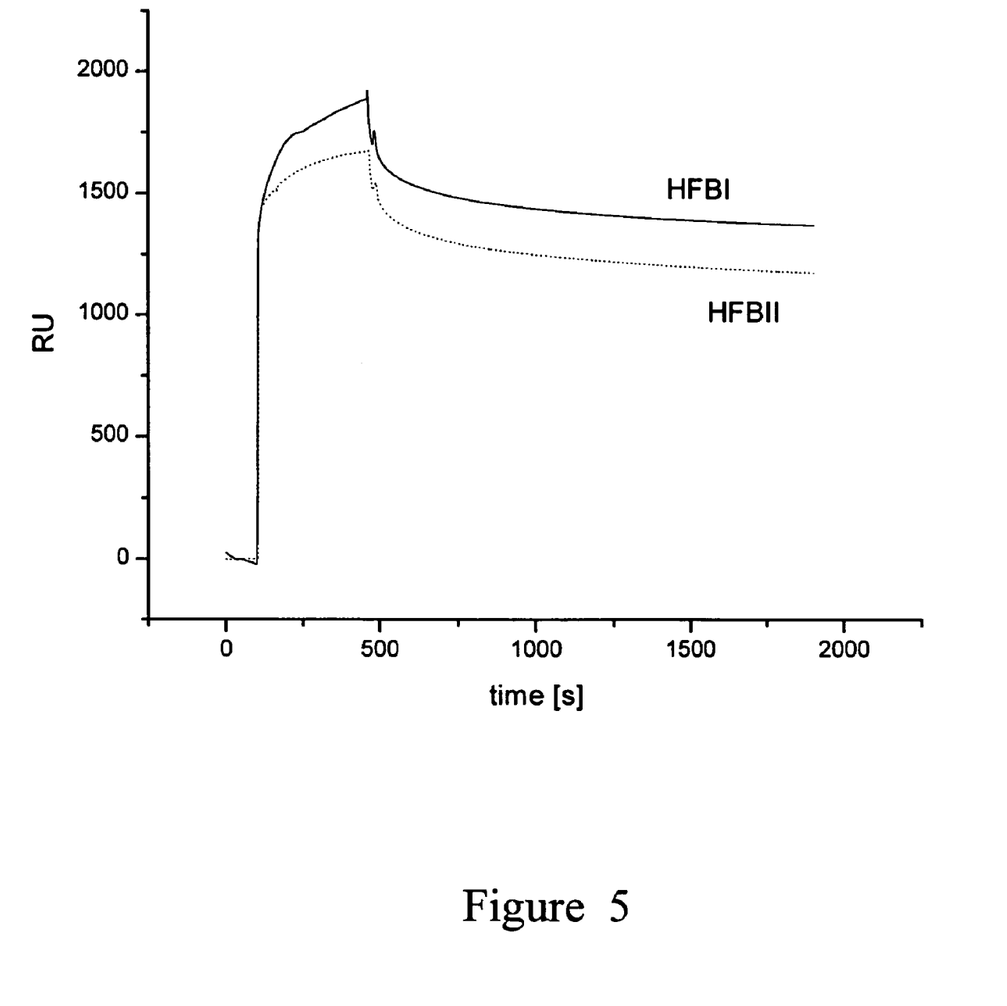
FIG. 5. Sensograms of native HFBI and HFBII binding to an alkylated gold surface measured by SPR. The free hydrophobins do not show the differences in binding seen when the hydrophobins are as parts of fusion proteins.

Additional tests using isolated hydrophobin are shown in FIG. 5. The curves obtained were not entirely smooth and from time to time gave an unstable response signal.

Nonetheless it can be seen that both proteins associate with the hydrophobic surface but HFBII had a slightly lower binding.

EXAMPLE 5

Ligand Density of Adsorbed Layer

Often it is important that the ligand density of the adsorbed layer can be optimized to a certain coverage. We show that by adding simultaneously free HFBI and the fusion protein EGI-HFBI, the two proteins adsorb in a stoichiometric ratio. The experiment was performed by having HFBI and fusion protein in a 1:1 ratio and in a 1:9 ratio in a tube and hydrophobic TEFLON or silanized glass stick immersed in the solution for 6 hours. After incubation the sticks were extensively washed and hydrolytic activity assayed by MUG2 as described in example 3. The bound activity was 50% of the control when the proteins were present in a 1:1 ratio and 10% with a 1:9 ratio. As a comparison the addition of an equal concentration of bovine serum albumin did not block the binding of the HFBI fusion to the silanized glass. Adding HFBI or HFBII in competition experiments resulted in the fusion protein being competed out at a stoichimetric ratio, as shown in FIG. 3A.

EXAMPLE 6

Binding Analyzed by Quartz Microbalance

The quartz crystal microbalance (QCM) used was a model QAFC 301 from Q-Sense (Sweden) which allows measurement of both frequency and dissipation factor (Hook, Rodahl et al. 1998). The quartz crystals had a resonance frequency of 5 MHz and were precoated with $SiO_2$ (QSX 303). The crystals were silanized with trimethylchlorosilane by incubating the reagent together with the sensor surface in an desiccator, and washed extensively with water. Protein (EGIc, EGIc-HFBI, and EGIc-HFBII) was diluted with 50 mM acetate buffer pH 5.0 to a concentration of 0.25–0.5 mg/ml. After a stable baseline had been established the sample was injected in the measurement chamber as described in (Hook, Rodahl et al. 1998) at a temperature of 30° C. $\Delta f$ and $\Delta D$ were recorded at 5 and 15 MHz at a sampling speed of 2 Hz.

Figure 6A:
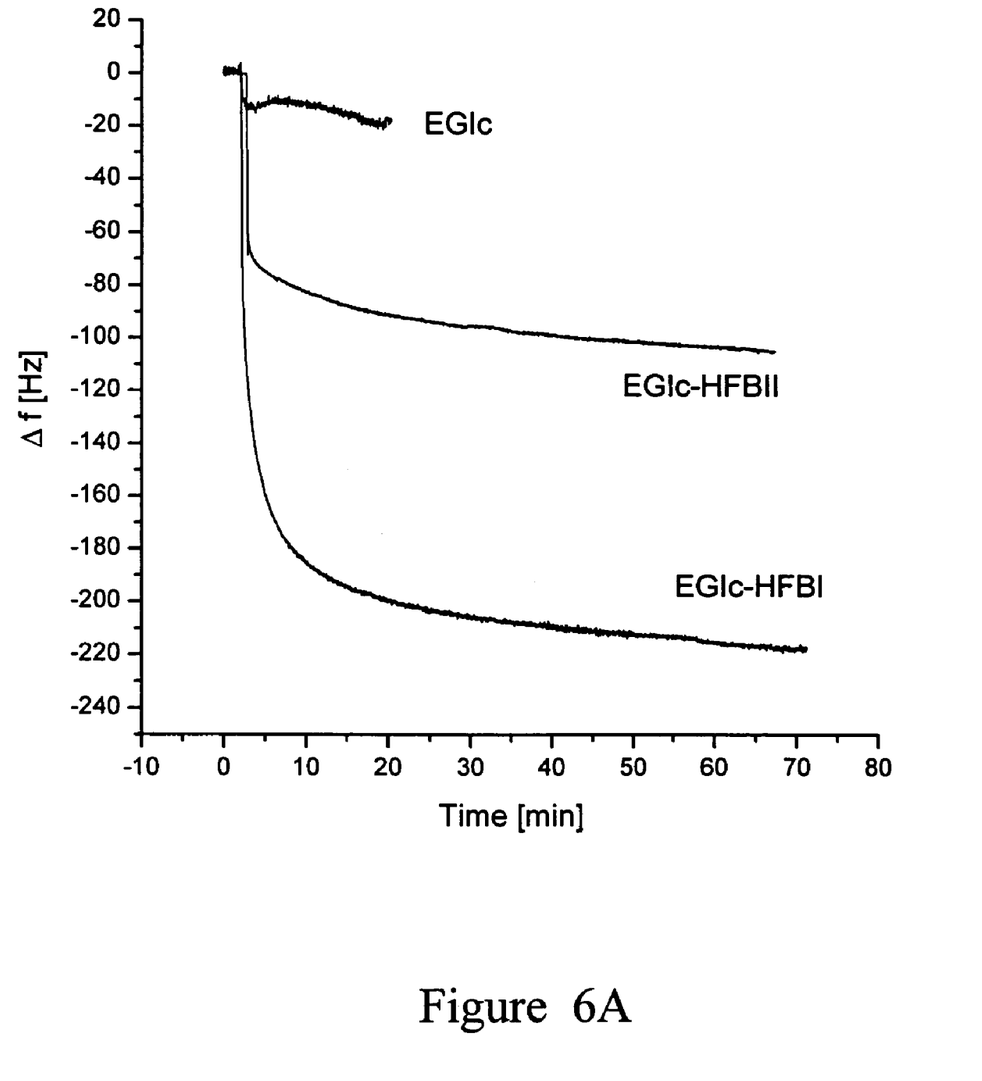

The quartz microbalance (QCM) gives two types of information. The change in frequency, $\Delta f$, is directly proportional to the adsorbed mass, and the dissipation change, $\Delta D$, gives information about the rate of dampening of the signal, which is dependant on the structure of the adsorbed layer. The adsorbed mass can be calculated from the change in resonant frequency by the Sauerbrey relation:

$$\Delta m = -C \Delta f / n$$

where $\Delta m$ is the adsorbed mass, n is the overtone number (n=1 for 5 MHz measurements and 3 for 15 MHz measurements), and C is the mass sensitivity constant (17.7 ng cm$^{-2}$ Hz$^{-1}$) (Sauerbrey 1959; Hook, Rodahl et al. 1998). FIG. 6 shows adsorption curves of the two fusion proteins and the control to a silanized quartz surface. EGIc-HFBI gives a maximal $\Delta f$ of 240 Hz, which corresponds to an adsorbed mass of 14 mg/m². In this measurement the free concentration of 0.25 mg/ml was saturating, as checked by titration with higher concentrations. Since the QCM has a sample cell in which the sample is static, and not flowing we see a situation for the HFBII fusion which corresponds to the injection phase in SPR. The results show that under an equilibrium situation the HFBII fusion binds to the hydrophobic surface.

Figure 6B:
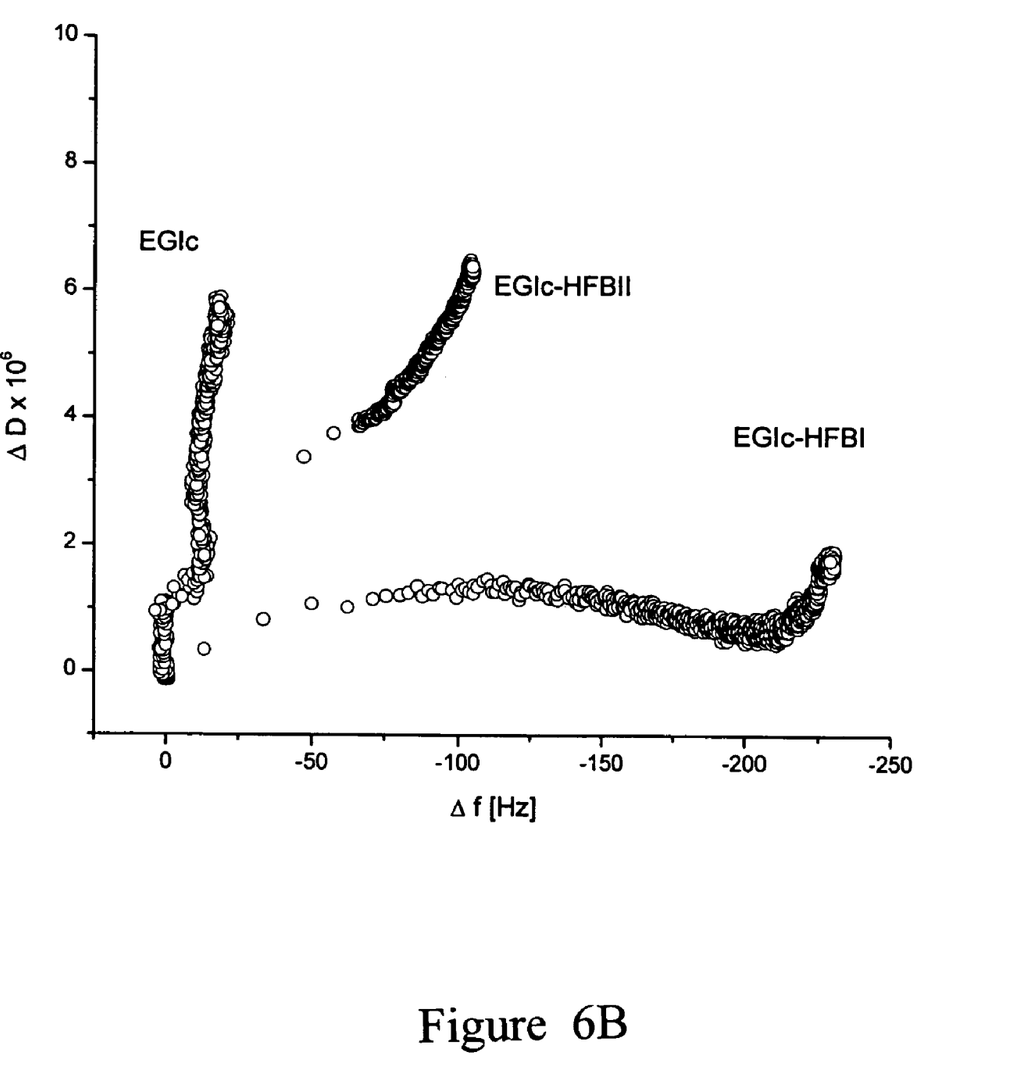

Plotting of $\Delta D$ as a function of $\Delta f$ gives information about the rigidity of the layer as a function of the adsorbed amount of protein. A small ΔD (slow dampening) indicates a rigid adsorbed layer and a large ΔD indicates an adsorbed layer which efficiently adsorbs the vibrational energy upon adsorption. From FIG. 6B we see that the EGIc layer associates very loosely with the surface, and gives a very steep curve with a big change in D for a very little change in f. The EGIc-HFBI binding shows a very large change in Δf which a corresponding small change in ΔD, which indicates that a dense and rigid layer is formed (Hook, Rodahl et al. 1998; Hook, Rodahl et al. 1998; Hook, Rodahl et al. 1998). The HFBII fusion shows an intermediate behavior. From the plot we can also see that the EGIc-HFBI adsorption is bi-phasic, with a small initial change in D which then becomes steeper closer to saturation. These data indicate that during the later stage of binding the layer grows in thickness as the protein packs tighter as saturation is approached. Usual dissipation values for globular proteins are about $1 \times 10^{-6}$ for a 20–40 change in f when they adsorb as a rigid layer (Hook, Rodahl et al. 1998; Hook, Rodahl et al. 1998; Hook, Rodahl et al. 1998). In the literature, higher values have been reported for example in the case of immunoglobulins bound to a layer of antigen, since this type of binding leaves the long Fc part hanging out into the solution.

EXAMPLE 7

Binding of Fusion Protein from a Crude Supernatant

TEFLON rods were immersed as described in example 3 in the culture medium in which EGIc-HFBI and EGIc-SC3 protein had been produced as described in example 2. As a control culture medium from the host strain not producing any fusion protein was used. Enzymatic assays showed that after a reaction time of 5 minutes the rods incubated in the control culture medium was not able to hydrolyze any MUG2 substrate, whereas the rods incubated in EGIc-SC3 hydrolyzed 0.15 μM of MUG2 and the rods incubated in EGIc-HFBI hydrolyzed 1.5 .mu.M of MUG2. The lower amount of activity on the EGIc-SC3 likely is due to the lower amount of this protein produced by *T. reesei* as compared to the EGIc-HIFBI.

EXAMPLE 8

Binding of Fusion Protein to Polystyrene Latex

The enzyme EGIc or the fusion protein EGIc-HFBI (100 μg/ml) was incubated in a suspension of latex beads (Sigma LB-30) for 3 hours. The suspension was then centrifuged at 10.000 g for 15 minutes so that the latex was pelleted, and the supernatant removed. The latex pellet was then resuspended in the original volume of buffer. Protein adsorption was followed by MUG2 activity (measured as in example 3) remaining in the supernatant, and activity on latex beads was measured from the resuspended latex pellet. The latex fraction for the EGIc protein showed no enzymatic activity whereas the EGIc-HFBI fusion protein incubated latex fraction showed an activity corresponding to 80% of the initial activity present in the incubation. In repeated experiments the activity of EGIc-HFBI bound to the latex beads showed no decrease in activity during four days of incubation in room temperature. In all cases, EGIc incubation with latex caused significant inactivation of the protein. The experiment shows that EGIc lost activity during incubation with latex beads probably due to denaturation, but the EGIc-HFBI did not but was functionally immobilized instead.

REFERENCES de Vocht, M. L., K. Scholtmeijer, et al. (1998). "Structural characterization of the hydrophobin SC3, as a monomer and after self-assembly at hydrophobic/hydrophilic interfaces." *Biophys. J.* 74(4): 2059–68.

de Vries, O., M. P. Fekkes, et al. (1993). "Insoluble hydrophobin complexes in the walls of *Schizophyllum communae* and other filamentous fungi." *Arch. Microbiol.* 159: 330–335.

De Vries, O. M., S. Moore, et al. (1999). "Identification and characterization of a tri-partite hydrophobin from *Claviceps fusiformis*. A novel type of class II hydrophobin." *Eur J Biochem* 262(2): 377–85.

Hashimoto, S. (2000). Principles of BIACORE. *Real time analysis of biomolecular interactions*. K. Nagata and H. Handa. Tokyo, Springer Verlag: 23–32.

Hook, F., M. Rodahl, et al. (1998). "Energy dissipation kinetics for protein and antibody-antigen adsorption under shear oscillation on a quarz crystal microbalance." *Langmuir* 14: 729–734.

Hook, F., M. Rodahl, et al. (1998). "QCM-measurements of ferritin monolayers on methyl-thiolated gold; depenence of energy dissipation and saturation coverage on salt concentration." *J Colloid Interface Sci* 208: 263–267.

Hook, F., M. Rodahl, et al. (1998). "Structural changes in hemoglobin during adsorption to solid surfaces: effects of pH, ionic strength, and ligand binding." *Proc Natl Acad Sci USA* 95(21): 12271–6.

Ianelli, C. J., Edson, C. M. et al. (1997) "A ligand for human CD48 on epithelial cells." Journal of Immunology 159(8): 3010–3920.

Lora, J. M., J. de la Cruz, et al. (1994). "A putative catabolite-repressed cell wall protein from the mycoparasitic fungus *Trichoderma harzianum*." *Mol Gen Genet* 242(4): 461–6.

Mach, R. L., M. Schindler, et al. (1994). "Transformation of *Trichoderma reesei* based on hygromycin B resistance using homologous expression signals." *Curr Genet* 25(6): 567–70.

Martin, G. G., G. C. Cannon, et al. (2000). "Sc3p hydrophobin organization in aqueous media and assembly onto surfaces as mediated be the associated polysaccharide schizophyllan." *Biomacromolecules* 1: 49–60.

Munoz, G., T. Nakari-Setala, et al. (1997). "Hydrophobin gene srh1, expressed during sporulation of the biocontrol agent *Trichoderma harzianum*." *Curr Genet* 32(3): 225–30.

Nakari-Setala, T., N. Aro, et al. (1997). "Differential expression of the vegetative and spore-bound hydrophobins of *Trichoderma reesei*—cloning and characterization of the hfb2 gene." *Eur. J. Biochem.* 248(2): 415–23.

Nakari-Setala, T., N. Aro, et al. (1996). "Genetic and biochemical characterization of the *Trichoderma reesei* hydrophobin HFBI." *Eur. J. Biochem.* 235(1-2): 248–55.

Penttila, M., H. Nevalainen, et al. (1987). "A versatile transformation system for the cellulolytic filamentous fungus *Trichoderma reesei*." *Gene* 61(2): 155–64.

Regimbald, L. H., Pilarski, L. M. (1996) "The breast mucin MUCI as a novel adhesion ligand for endothelial intercellular adhesion molecule 1 in breast cancer". Cancer Research 56(18): 4244–49.

Sauerbrey (1959). "Verwendung von Schwingquarzen zur Wargung dunner Schichten zur Mikrowagung." *Z. Physik* 155: 206–222.

Srisodsuk, M., J. Lehtio, et al. (1997). "*Trichoderma reesei* cellobiohydrolase I with an endoglucanase cellulose-binding domain: action on bacterial microcrystalline cellulose." *J Biotechnol* 57(1-3): 49–57.

Wessels, J. G. (1997). "Hydrophobins: proteins that change the nature of the fungal surface." *Adv. Microb. Physiol.* 38: 1–45.

Wessels, J. G. H. (1996). "Fungal hydrophobins: proteins that function at an interface." *Trends Plant Sci.* 1(1): 9–15.

Wosten, H. A. and M. L. de Vocht (2000). "Hydrophobins, the fungal coat unravelled." *Biochim Biophys Acta* 1469 (2): 79–86.

Wosten, H. A. B., O. M. H. de Vries, et al. (1993). "Interfacial self-assembly of a fungal hydrophobin into a hydrophobic rodlet layer." *Plant cell* 5: 1567–1574.

The invention claimed is:

1. A process for immobilizing one or more polypeptides as a fusion polypeptide, comprising the steps:
   (A) fusing a nucleotide sequence encoding an adhesion polypeptide to a nucleotide sequence encoding a preselected polypeptide to form a fusion construct, wherein the adhension polypeptide is Class II hydrophobin;
   (B) expressing the fusion construct in a host under suitable conditions;
   (C) applying the fusion polypeptide directly from the growth medium or from purified or from partly purified growth medium or from broken host cells or from unpurified, purified or a partly purified protein solution, to a solid surface, thereby immobilizing the polypeptide through the adhesion polypeptide fused thereto.

2. The process according to claim 1, wherein the preselected polypeptide has at least 50% of the biological function or activity in immobilized form that it has in its free form.

3. The process according to claim 1, wherein the adhesion polypeptide is a *Trichoderma* hydrophobin.

4. The process according to claim 1, wherein the hydrophobin is *Trichoderma reesei* HFBI, *Trichoderma reesei* HFBII, or *T. harzianum* SRHI.

5. The process according to claim 1, wherein the solid surface is hydrophobic.

6. The process according to claim 1, wherein the solid surface is selected from the group consisting of a silanized surface, a hydrocarbon coated surface, and a polymer surface.

7. The process according to claim 1, wherein the immobilization of the fusion polypeptide to the solid surface is spontaneous.

8. The process according to claim 1, wherein the fusion polypeptide can be desorbed from the surface in a controlled fashion.

9. The process according to claim 1, wherein the fusion polypeptide is immobilized together with a specific amount of free adhesion polypeptides.

10. The process according to claim 1, wherein the preselected polypeptide is oriented out from the surface.

11. The process according to claim 1, wherein two or more preselected polypeptides are immobilized as fusion constructs to the same solid surface.

12. The process according to claim 1, wherein the fusion polypeptide is produced in a fungal or yeast host selected from the group consisting of *Trichoderma* spp, *Aspergillus* spp. *Neurospora* spp., *Fusarium* spp., *Penicillium* spp., *Humicola* spp., *Tolypocladium geodes, Kluyveromyces* spp., *Pichia* spp., *Hansenula* spp., *Candida* spp., *Yarrowia* spp, *Schizosaccharomyces* ssp, *Saccharomyces* spp. and *Schizophyllum* spp.

13. The process according to claim 12, wherein the fungal host is *Trichoderma* spp.

14. The process according to claim 1, wherein the immobilization is carried out at a temperature of 5 to 40° C.

15. The process according to claim 1, wherein the immobilization is carried out at pH 3 to 7.

16. The process according to claim 1, wherein the immobilization is carried out at an ionic strength of 0.1 to 2 M.

17. The process according to claim 14, wherein the immobilization is carried out at a temperature of 20° C. to 35° C.

18. The process according to claim 15, wherein the immobilization is carried out at a pH 4 to 6.

19. The process according to claim 16, wherein the immobilization is carried out at an ionic strength of 0.5 to 1 M.

20. The process according to claim 6, wherein said polymer is polyetene, polypropylene, polystyrene or TEFLON.

* * * * *